United States Patent [19]

Ferlazzo et al.

[11] 4,388,223

[45] Jun. 14, 1983

[54] CATALYST FOR THE CONVERSION OF UNSATURATED HYDROCARBONS INTO DIOLEFINS OR UNSATURATED ALDEHYDES AND NITRILES, AND PROCESS FOR PREPARING THE SAME

[75] Inventors: Natale Ferlazzo, Segrate; Natale Bertolini, Milan; Marcello Ghirga, Bresso, all of Italy

[73] Assignee: Euteco Impianti S.p.A., Milan, Italy

[21] Appl. No.: 251,434

[22] Filed: Apr. 6, 1981

[51] Int. Cl.³ .................... B01J 23/10; B01J 23/34; B01J 23/86; B01J 23/88
[52] U.S. Cl. .................... 252/437; 252/439; 252/455 R; 252/457; 252/458; 252/462; 252/464; 252/465; 252/467; 252/468; 252/470
[58] Field of Search .............. 252/467, 470, 437, 439, 252/455 R, 457, 458, 462, 464, 465, 468

[56] References Cited

U.S. PATENT DOCUMENTS

| | | | |
|---|---|---|---|
| 3,855,308 | 12/1974 | Ueshima et al. | 252/455 R |
| 3,911,039 | 10/1975 | Grasselli et al. | 252/470 X |
| 4,166,808 | 9/1979 | Daumas et al. | 252/470 X |
| 4,192,776 | 3/1980 | Grasselli et al. | 252/470 X |

*Primary Examiner*—W. J. Shine
*Attorney, Agent, or Firm*—Sughrue, Mion, Zinn, Macpeak and Seas

[57] ABSTRACT

The catalyst comprises one or more molybdates of trivalent metals chosen from Fe, Al, Ce and Cr and/or molybdates of bivalent metals chosen from alpha manganese molybdate, beta cobalt molybdate, beta nickel molybdate and the molybdates of Zn, Mg and Ca, and one or more promoter elements chosen from Se, Te, As, Sb, V, Nb, Sn, Pb and Tl homogeneously distributed within the crystalline structure of said molybdates with distortion thereof without creating new crystalline phases.

19 Claims, No Drawings

CATALYST FOR THE CONVERSION OF UNSATURATED HYDROCARBONS INTO DIOLEFINS OR UNSATURATED ALDEHYDES AND NITRILES, AND PROCESS FOR PREPARING THE SAME

The present invention relates to a catalyst active in the conversion of unsaturated hydrocarbons, and a process for the conversion of unsaturated hydrocarbons in the presence of such a catalyst. The invention also relates to a process for the preparation of said catalyst.

In the following description, by "unsaturated hydrocarbons" there will be meant hydrocarbon compounds carrying one or more methyl or methylene reactive groups in the alpha position with respect to an aliphatic or aromatic double bond. By "conversion" of the unsaturated hydrocarbons there will be meant the transformation of the said unsaturated hydrocarbons into the corresponding unsaturated nitriles (by reacton with ammonia and oxygen, oxyammoniation), or the oxidation of the said unsaturated hydrocarbons into the corresponding unsaturated aldehydes, or their oxidizing dehydrogenation into the corresponding diolefins. Typical examples of unsaturated hydrocarbons according to the invention are propylene, isobutene, xylene, and butene-1. Examples of conversion of said unsaturated hydrocarbons are the oxyammoniation of propylene, isobutene and xylene to acrylonitrile, methacrylonitrile and respectively dinitrilebenzene, the oxidation of propylene or isobutylene to acrolein or respectively methacrolein, and the oxidizing dehydrogenation of butene-1 to butadiene.

As is known, the conventional catalysts active in the oxyammoniation reactions, especially of propylene, generally contain molybdenum and phosphorus, together with bismuth, tin and/or antimony in the form of oxides. Molybdenum may be replaced by tungsten, and phosphorus may be partially replaced by arsenic. The catalyst under discussion may additionally contain one or more oxides of further elements such as iron, nickel, cobalt, alkali metals, alkaline earth metals and rare earths. Reference is made in this connection to Italian Pat. No. 605,134, British Pat. No. 884,437, U.S. Pat. No. 3,859,358 and West Germany Patent Application Publication No. 2,147,480.

Various catalysts, generally described as mixed metallic oxides and especially suitable for the oxidation of propylene to acrolein, are also known in the art. A particularly important class of such known catalysts includes an essential elements molybdenum, bismuth and phosphorus in the form of oxides. Further possible constitutents of the catalysts under discussion are the oxides of iron, nickel and/or cobalt, arsenic (this last replacing partially or wholly phosphorus) and alkali and/or alkaline earth metals. Reference is made in this connection to U.S. Pat. Nos. 3,171,859 and 3,522,299, Italian Pat. No. 729,694 and West Germany Patent Application Publications Nos. 2,020,791 and 2,038,749.

Catalysts active in the oxidizing dehydrogenation of olefins to diolefins are also known in the art, for example those based on oxides of antimony and cerium, or antimony and manganese, as described in U.S. Pat. Nos. 3,251,900 and 3,257,474. Other suitable catalysts contain oxides of phosphorus, molybdenum and bismuth and possibly also oxides of further metals, such as iron, cobalt, nickel, antimony, boron and alkali metals. Reference is made in this connection to British Pat. No. 999,859 and Dutch Patent Application Publications Nos. 66/07790 and 70/15093.

The known catalysts based on metallic oxides are prepared by means of a process which generally comprises the precipitation of the oxides from corresponding soluble salts, a drying of the thus obtained precipitate and a thermal treatment at elevated temperature of the dried precipitate. Few attempts have been made in the art to influence the behaviour of said catalysts as a function not only of their chemical composition, but also of their crystalline form, their surface characteristics and their physical form. By behaviour of the catalyst, there are meant the activity and selectivity values, and the mechanical resistance properties, achieved in the catalytic process and under the utilization conditions. As a result, it is often difficult, when using conventional preparation processes, to obtain catalysts with reproducible characteristics. Moreover, the metallic oxide catalysts are often of little interest for use in commercial processes, owing to their poor mechanical properties and wear resistance and their tendency to liberate powders. Further important characteristics of the catalysts under discussion are the activity and selectivity achieved in the processes in which they are used. As a general rule, any increase in conversion of the reagents corresponds to a decrease in conversion into useful reaction products, i.e., a decrease in selectivity value. The difficulties encountered in attempting to achieve both high conversion values and high selectivity values with the same catalyst, are well known to the skilled artisans.

An object of the present invention is to overcome the drawbacks inherent to the use of the conventional catalysts in the conversion of unsaturated hydrocarbons.

A particular object of the present invention is the achievement of catalysts which present high activity and selectivity values in the conversion of unsaturated hydrocarbons, together with a high mechanical resistance.

A further object of the invention is a process for the conversion of hydrocarbons in the presence of said catalysts.

Another object of the invention is a process for the preparation of said catalysts.

Further objects of the invention will result from the following description.

Accordingly, the present invention provides a catalyst active and selective in the processes for the conversion of unsaturated hydrocarbons, and mechanically resistant under the utilization conditions, said catalyst comprising:

a crystalline phase (I) consisting of one or more molybdates belonging to the monoclinic system, chosen from ferric molybdate and the molybdates, isomorphs of ferric molybdate, of the following trivalent elements: aluminum, cerium and chromium; and/or a crystalline phase (II) consisting of one or more molybdates belonging to the monoclinic system, chosen from alpha manganese molybdate and the following molybdates of bivalent elements, isomorphs of alpha manganese molybdate: beta cobalt molybdate, beta nickel molybdate and the molybdates of zinc, magnesium and cadmium; and one or more promoter chemical elements, having a capability of change in valency of at least two electrons, with electronegative properties in the higher state of valency, chosen from selenium, tellurium, arsenic, antimony, bismuth, vanadium, niobium, tin, lead and thallium; said promoter element being homogeneously distributed within the crystalline phases (I) and/or (II) with distortion of the structure of said phases (I) and/or (II) without creating new further phases.

When it is desired to use the catalyst in the form of a fluidized bed, said catalyst should preferably be in the form of particles with an average size of from 5 to 200 microns, with an apparent density of from 0.6 to 1.2 g/ml, and with a specific surface area higher than 10 m$^2$/g, up to 150 m$^2$/g.

The use of a fluidized bed of catalyst is generally preferred in the case of the conversion of the unsaturated hydrocarbons into unsaturated nitriles.

When it is desired to use the catalyst in the form of a fixed bed, a fine powder of said catalyst may be compressed into bodies of the desired size, with an apparent density of from 0.8 to 1.5 g/ml and with a specific surface area of from 1 to 10 m$^2$/g. The use of a fixed bed of catalyst is generally preferred in the case of the conversion of the unsaturated hydrocarbons into unsaturated aldehydes or diolefins.

The behaviour of the catalyst in the conversion of the unsaturated hydrocarbons depends not only on its chemical composition but also on its crystalline structure, its surface characteristics and its physical form. According to the present invention, by means of a suitable correlation between these characteristics the behaviours of the catalysts thus obtained are surprisingly improved in their use in said conversion processes.

The catalyst of the present invention comprises one or two crystalline phases, and at least one modifying element.

More particularly, the crystalline phase (I) consists of one or more metallic molybdates belonging to the monoclinic system and to the crystallographic class the chief member of which is ferric molybdate. These molybdates may be defined by means of the general formula $Me_2^{(III)}(MoO_4)_3$, wherein $Me^{(III)}$ is iron, aluminium, cerium or chromium. Moreover, the crystalline phase (II) consists of one or more molybdates belonging to the monoclinic system and to the crystallographic class the chief member of which is alpha manganese molybdate. These molybdates may be defined by means of the general formula $Me^{II}MoO_4$, wherein $Me^{II}$ is manganese, cobalt, nickel, zinc, magnesium or cadmium.

The catalysts of the present invention may comprise only one of the two phases indicated above. However, in the preferred embodiment, the crystalline phases (I) and (II) are simultaneously present in the catalyst as separate substances. In this last case, the molar ratio between phase (I), expressed as $Me_2^{III}(MoO_4)_3$, and phase (II), expressed as $Me^{II}MoO_4$, is conveniently from 0.1:1 to 5:1, preferably from 0.2:1 to 1:1.

It should be noted that the crystalline phases (I) and (II) alone or in mixture, do not show any appreciable catalytic activity in the conversion of unsaturated hydrocarbons in the absence of the aforesaid promotors. As already indicated, said promoters are chemical elements with electronegative characteristics in the higher state of valency, in which the valency may change by at least two electrons. In particular, these elements are chosen from selenium, tellurium, arsenic, antimony, bismuth, vanadium, niobium, tin, lead and thallium. The introduction of the promoters into the crystalline phases may be carried out by adding said promoters during the preparation of said crystalline phases. The said introduction may also be carried out after the preparation of the crystalline phases, for example by infiltration. Conveniently, when the crystalline phases are prepared by precipitation, the promoters may be added as coprecipitates.

Even if their arrangement within the crystalline phases is not completely known, it is probably that said promoters partially replace one or more elements in the crystalline lattice of phases (I) and/or (II), and/or occupy free internal sites of said crystalline lattice. In each case, it is essential for the purposes of the present invention that the introduction of the promoting elements be carried out without giving rise to the formation of further new crystalline phases.

To this end, the atomic ratio between atoms of said promoters and the overall number of atoms $Me^{(III)}+Me^{(II)}$ in the phases (I) and (II) is generally maintained to values of from 0.01:1 to 1.0:1. The best results are generally obtained with an atomic ratio of from 0.05:1 to 0.5:1.

It was analytically ascertained that the introduction of the promoters brings about a distortion or deformation of the crystalline lattice of phases (I) and/or (II), as shown by the shifting or broadening of the bands at analysis by X-ray diffractometer. These effects, which may be promoted by using particular expedients in the preparation of the catalysts, constitute an essential condition for obtaining catalysts with the highest possible characteristics.

It should also be noted that crystalline phases (I) or (II) containing promoters different from those indicated above, are little active and selective in the conversion of unsaturated hydrocarbons. Surprisingly, the phases (I) and/or (II) modified according to the present invention give rise to catalysts which permit conversion and selectivity values of at least 80-90% to be obtained in the aforesaid conversion of the unsaturated hydrocarbon, for periods of use which are very interesting from the industrial viewpoint. As already indicated, these desirable results depend also on the physical form and surface characteristics of the catalytst, which depend in turn on the intended use of said catalyst.

More particularly, when it is intended to use the catalyst in the form of a fluidized bed, said catalyst is preferably in the form of granules with an average size of from 5 to 200 microns, with an apparent density of from 0.6 to 1.2 g/ml, obtained for example by spray-drying or by impregnation of a suitable support; the specific surface area of said granules is generally from 10 to 150 m$^2$/g, preferably from 15 to 110 m$^2$/g, the desired values being obtained by suitable control of the operating conditions in the preparation in the catalyst.

When it is desired to use the catalyst in the form of a fixed bed, said catalyst is formed into bodies with an apparent density of from 0.8 to 1.5 g/ml by compression of powders; the specific surface area of said bodies is generally from 1 to 10 m$^2$/g, and largerly depends on the degree of compactness of said powders.

These aspects will be illustrated in detail in the description of the preparation process of the catalyst.

In some cases the catalyst of the present invention may conveniently comprise alkaline elements (such as potassium, lithium, cesium and magnesium) and/or acidic elements (such as phosphorus and silicon) in order to optimize the degree of activity of the active centers, especially the surface centers. Generally, the amount of basic or acid elements ranges from 0.005 to 0.5 atoms for each atom of molybdenum. The said basic and acid elements may be added before, during or after the preparation of the crystalline phases. Conveniently, in the case of the preparation of the crystalline phases by precipitation, said basic and acid elements are added at the precipitation step.

The catalyst of the present invention may also contain amorphous silica in amounts up to 50% by weight on the catalyst. Said silica may be used as a support or a diluent, or to influence the degree of activity of said active centres. The silica may be used, for example, in the case of a fixed bed of catalyst, in percentages generally not exceeding 20 wt.%, or in the conversion of said unsaturated hydrocarbons into aldehydes or olefins.

The catalyst of the present invention may be prepared by means of a process comprising the following series of steps:

precipitation from soluble compounds of the metals, especially nitrates and ammonium salts, in an aqueous medium, while increasing the pH value from an initial value of about 1 to a final value of about 5.5;

drying of the precipitate thus obtained with reduction of its water content to values lower than about 5-10% by weight; this treatment may be carried out by spray-drying and, if desired, formation of granules with an average size of from 5 to 200 microns;

thermal treatment of the dried precipitate at a temperature of from 250° to 420° C. for a period sufficient to decompose substantially completely the anions (nitrates and ammonium salts) present therein;

possible compaction of the product obtained at the thermal treatment step, into bodies of the desired size;

thermal activation of the granules thus treated at a temperature of from 500° to 750° C.

Compounds suitable for the preparation of the catalyst are ammonium paramolybdate and the nitrates of the trivalent and bivalent elements of phases (I) and (II) respectively. As regards the promoting elements, use is generally made of the corresponding acids and/or oxides of said elements in their highest degree of valency or, in the absence of the latter, of the corresponding nitrates.

The precipitation may be carried out by using aqueous solutions of said compounds in deionized water, which are mixed at a temperature of from 20° to 130° C., at atmospheric pressure or under a light overpressure (for example up to 5 kg/cm$^2$).

In a preferred embodiment an aqueous solution of ammonium paramolybdate is mixed, at a temperature of the order of 80° C., with a mixture of fused nitrates of the elements Me$^{II}$ and/or Me$^{III}$. The promoter element is dissolved in the aqueous solution of ammonium paramolybdate, when said element is in the form of an acid or an oxide, or else in the fused mass when it is in the form of a nitrate. The precipitation is typically initiated at a pH value of about 1 and then ammonia is added to the agitated mass heated at about 80° C. over a period of about 2 hours, until the pH value is brought to about 5.5. The formation of precursors of the desired crystalline phases is promoted by using in the precipitation a solids concentration in the suspension of the order of 20-40% by weight. To this end the concentration of the starting solutions is set to suitable values, or suitable dilutions with deionized water are carried out during the precipitation operations. Obviously, the relative amounts of the compounds used are such as to obtain the desired composition in the final catalyst.

The drying of the resulting precipitate is such as to completely remove the water, or at least to reduce its content to values lower than about 5-10% by weight. The removal of the water may be carried out by using a spray-drying. In this case the suspension of the precipitate is sprayed into a suitable apparatus, in countercurrent with hot air. Typically, there is discharged from the apparatus a microspheroidal fine powder with a moisture content not exceeding 5% by weight.

The drying temperature used is lower than those which bring about decomposition of the solids. Typically, said temperature is of the order of 100°-180° C., referred to the solid.

When using the spray-drying technique, the conditions may be such as to obtain granules with a size of the order of 5-200 microns, particularly suitable for use as a fluidized bed, or granules with a size of the order of 1-10 microns, particularly suitable for the subsequent forming into bodies for use as a fixed bed. In each case, these sizes are particularly suitable for the subsequent decomposition of the nitrates and the ammonium salts. When the drying is carried out by means of a different technique, it is convenient to grind the dried solid to the desired average size, for example to a size lower than about 50 microns.

The dried granules thus obtained are submitted to a thermal treatment in air by bringing the temperature to values of from 250° to 420° C., and by keeping said granules under these conditions for a period sufficient to permit a substantially complete decomposition of the nitrates or the ammonium salts. According to a typical embodiment, the temperature of the granules is gradually increased (period of the order of 3-20 hours) from the drying temperature up to the value chosen for the decomposition (within the range indicated) and the temperature is maintained at this pre-chosen value for 1-2 hours. All these operations are carried out in air.

At this point, the granules obtained at the thermal decomposition treatment may possibly be submitted to a compaction treatment to form said granules into bodies of the suitable size, utilizable in the conversion reactions in the form of a fixed bed. Thus, according to a typical embodiment, the granules obtained at the decomposition step are saturated with water, using a solid/water weight ratio of the order of 100:5. The cake thus obtained is dried and then reduced to granules with a size generally of the order of 0.1-1 mm. A lubricant such as stearic acid and/or magnesium stearate is added to the granulate in an amount of about 0.5-2% by weight, and the compaction is carried out in suitable apparatus used in the art for the compaction of granular solids. The granulate may be formed into spherical or cylindrical bodies, or preferably into rings having typically the following dimensions: height 5 mm, outer diameter 5 mm and bore diameter 1.8-2 mm.

The compaction treatment of the powders described above is important, in the sense that it permits desired properties to be conferred on the catalyst. In particular, the mechanical resistance of said compacted solids is such as to allow their conversion into the final catalyst without any danger of fracture, powdering and similar; moreover, the density and surface area of the catalysts are set to the desired values by means of the compaction treatment (especially through control of the pressure load). Generally, the pressure load used in the compaction is from 1 to 2 tons. Moreover, in the case of the use of lubricants, the latter are suitably decomposed by heating of the compacted solid in an oven with air circulation, at a temperature not exceeding 420° C.

The granules submitted to the decomposition treatment and optionally to the compaction treatment, are activated by heating at high temperature, generally at 500°–750° C., preferably 500°–600° C. This treatment is carried out in the presence of air, and for a period of from 2 to 8 hours, depending on the pre-chosen temperature. Upon cooling, there is obtained the final catalyst with characteristics within the ranges already indicated.

When it is desired to obtain a catalyst containing amorphous silica, a soluble silicate is added to the precipitation medium. In particular, said silicate, such as ammonium silicate, may be added to the solution of metallic salts. The silicate may be chosen from the products known as soluble silica, or ammoniacal soluble silica, for example the commercial product "Ludox AS". Satisfactory results are obtained by using aqueous solutions with an overall solids content of the order of 20–40% by weight. The solution thus obtained is submitted to spray-drying treatment with formation of microspheroidal particles which are then submitted to the decomposition treatment and the thermal activation treatment already indicated. By operating in this manner, there is obtained a catalyst containing amorphous silica as a diluent, and the latter may be present in the catalyst in amounts up to 50% by weight.

According to a further embodiment, the solutions of metallic salts are used to impregnate microspheroidal silica. In this case, it is preferable to use a silica in the form of particles with a size of from 5 to 200 microns, with a surface area of from 20 to 700 m$^2$/g, an overall pore volume of from 0.5 to 1.5 ml/g and an apparent density of from 0.25 to 1 g/ml. The impregnated product is then dried, generally at a temperature of about 120°–130° C., and the decomposition and thermal activation treatments are then carried out as indicated above. In this case the quantity of support in the final catalyst may reach values of the order of 80% by weight.

As already indicated, the catalyst of the present invention may be used in the conversion of unsaturated hydrocarbons.

Thus, for example, the oxyammoniation reaction of unsaturated hydrocarbons may be carried out by using a fluidized bed of catalyst arranged in a suitable reactor, operating under the following conditions:

there is passed through the catalyst a gaseous stream containing 3–8% in volume of unsaturated hydrocarbons, 3–8% in volume of ammonia, 15–18% in volume of oxygen, the remaining percentage consisting of inert gases such as nitrogen, steam, carbon dioxide and the like;

the reaction is carried out at a temperature of from 350° to 450° C., preferably from 400° to 440° C., without applying any overpressure, or by using a light overpressure up to 1 kg/cm$^2$;

the residence time is generally maintained at a value of from 1 to 20 seconds.

By operating under these conditions and by using propylene as the unsaturated hydrocarbons, the conversion is typically of the order of 95–100%, with a selectivity for acrylonitrile of the order of 80–90%. The stability of the catalyst is such as to allow its use under the operation conditions for industrially interesting periods.

The oxidation reaction of the unsaturated hydrocarbons may be carried out by using a fixed bed of catalyst arranged in a suitable reactor, and by operating under the following typical conditions:

there is passed through the catalyst a gaseous stream containing 4–7% in volume of unsaturated hydrocarbons, 8–13% in volume of oxygen, the remaining percentage consisting of inert compounds such as steam, nitrogen and carbon dioxide;

the molar ratio between oxygen and unsaturated hydrocarbon in the feed is conveniently maintained at a value of from 1.3:1 to 2.5:1, and preferably from 1.5:1 to 2.0:1;

the reaction is carried out at a temperature of from 320° to 450° C., preferably 350°–400° C., without applying any overpressure, or under a light overpressure, for example up to about 2 kg/cm$^2$;

the contact time is of the order of 2–4 seconds.

By operating under these conditions and by using propylene as the unsaturated hydrocarbon, the conversion is typically higher than 95%, with a selectivity for acrolein of the order of about 90% or more. Again, the stability of the catalyst is such as to allow its use under the operating conditions for industrially interesting periods. The catalyst is preferably in the form of rings, which permit, among others, the reaction to be carried out with a low head loss between the two ends of the catalytic bed.

The following experimental examples are illustrative and non-limitative for the invention.

EXAMPLE 1

45 g of telluric acid are added to a solution of 211.86 g of ammonium paramolybdate $(NH_4)_6Mo_7O_{24}.H_2O$ and 6.5 of dibasic ammonium phosphate, dissolved at 80° C. in 500 ml of deionized water. The solution is cooled down to 35° C., and there are gradually added 50 ml. of 36% (weight/volume) hydrogen peroxide, corresponding to a titre of 120 volumes. The solution thus obtained is admixed with a solution formed of 130.3 g of cerium nitrate hexahydrate $Ce(NO_3)_3.6H_2O$, 40.4 g of iron nitrate nonohydrate $Fe(NO_3)_3.9H_2O$, 14.55 g of cobalt nitrate hexahydrate $Co(NO_3)_2.6H_2O$, 14.54 g of nickel nitrate hexahydrate $Ni(NO_3)_6.6H_2O$, 12.5 g of manganese nitrate tetrahydrate $Mn(NO_3)_2.4H_2O$ and 1.02 g of potassium nitrate $KNO_3$, dissolved in 400 ml. of deionized water.

The resulting solution is added dropwise to one kg of microspheroidal silica with a size of 10–150 microns, a porosity of 1 ml/g and a surface area of 500 m$^2$/g. The whole is homogenized, to uniformly impregnate the silica, and drying is then carried out at 130° C. for 12 hours to reduce the water content to values of the order of 5–10% by weight. The granules are then heated in the presence of air, by increasing the temperature by 20° C. each hour, starting from the drying temperature and up to 420° C., and the temperature is maintained at this last value for one hour. The temperature is then increased by 20° C. each hour up to 510° C., and is maintained at this last value for 3 hours in the presence of air.

The catalyst thus obtained, suitable for use as a fluidized bed, has the following characteristics:

size of from 10 to 150 microns
apparent density: 0.6 g/ml
specific surface area: 103 sq.m/g The catalyst has a support content (amorphous silica) equal to 70% by weight.

As regards the active part of the catalyst, the molar ratio between phase (I) and phase (II), as defined above, is equal to 1.333:1. Moreover, the atomic ratio between promoter and the sum of the metals Me$^{II}$ and Me$^{III}$ is equal to 0.3636:1. The quantity of acid element (phosphorus) and basic element (potassium) is equal to 0.042 and respectively 0.0083 atoms for each atom of molybdenum.

Analysis of the catalyst by infra-red spectrometry and X-ray diffractometry shows a structure isomorphous to that of ferric molybdate crystallized in the monoclinic system, and the structure of beta cobalt molybdate isomorphous to that of alpha manganese molybdate, in addition to a slight shifting and broadening of the diffraction bands, attributable to the insertion of tellurium into the crystalline lattices, either in the interstices or in replacement of other atoms.

EXAMPLE 2

1.5 liters of the catalyst prepared in Example 1 are charged into a steel reactor with a diameter of 62.5 mm, provided at the bottom with a distribution plate of sinterized steel, and 9 foraminous plates (each with 60 holes 3 mm in diameter) arranged transversely on suitable bearings at a distance of 60 mm from each other.

The reactor is fed with a gaseous mixture having the following composition in volume:
 oxygen: 17.8%
 nitrogen: 67.3%
 propylene: 7.1%
 ammonia: 7.8%

By operating under fluidization conditions at 430° C., without applying any overpressure, with a contact time of 4.2 seconds, and a linear gas velocity of 120 cm/sec., there is obtained a propylene conversion of 98.3% with a selectivity for acrylonitrile of 87% based on the converted propylene.

EXAMPLE 3

The following mixture of hydrates is dissolved in its crystallization water:
 $Bi(NO_3)_3.5H_2O$—170.499 g
 $Fe(NO_3)_3.9H_2O$—284.014 g
 $Cr(NO_3)_3.9H_2O$—140.647 g
 $Co(NO_3)_2.6H_2O$—511.483 g
 $Ni(NO_3)_2.6H_2O$—204.432 g 744.67 g of ammonium paramolybdate are dissolved at 95° C. in 1500 ml of deionized water, and the whole is cooled to 80° C. There are then added 20.27 g of 85 wt.% phosphoric acid (brought to pH 4 by addition of dilute aqueous ammonia), 250.76 g of colloidal silica LUDOX AS containing 40% by weight of $SiO_2$, and 47.77 g of $K_2H_2Sb_2O_7.6H_2O$. The mixture of nitrates indicated above is gradually added to this solution over about 20 minutes. The resulting suspension, having a pH of about 1.5 is maintained at 80° C. under agitation, and aqueous ammonia is gradually added to set and maintain the pH at a value of 5.5. The mixture is maintained at 80° C. for a further 3.5 hours. The suspension, having a solids content of the order of 25% by weight, is spray-dried in countercurrent with air having an inlet temperature of 200° C. and an outlet temperature of 130° C. There are thus obtained microspheroidal particles with a size of from 10 to 150 microns and a water content of the order of 5% by weight, which are heated in the presence of air up to 420° C., gradually and in 12 hours, and then maintained at 420° C. for one hour.

The particles are then activated by heating in an oven in the presence of air, by increasing the temperature by 50° C. each hour up to a final value of 540° C. and maintaining the temperature at 540° C. for 4 hours.

The catalyst thus obtained has a diluent content (amorphous silica) equal to 10% by weight, and the following characteristics:
 apparent density: 1.2 g/ml
 specific surface area: 21 sq.m/g.

The molar ratio between phases (I) and (II) in the catalyst is equal to 0.215:1, expressed as defined above, and the atomic ratio between promoters and the sum of the metals $Me^{II}$ and $Me^{III}$ is equal to 0.15:1. The quantity of acid element (phosphorus) and basic element (postssium) is equal to 0.083 and respectively 0.042 atoms for each atom of molybdenum.

Analysis by X-ray diffractometry and infra-red spectometry shows a phase isomorphous to alpha manganese molybdate, and the phase isomorphous to ferric molybdate crystallized in the monoclinic system, with a slight shifting and broadening of the bands due to the insertion of the promoters.

EXAMPLE 4

1.5 liters of the catalyst obtained in Example 3 are charged into a fluid bed steel reactor, with a diameter of 62.5 mm, provided at the bottom with a distribution plate of sinterized steel, and 9 foraminous plates (each with 60 holes 3 mm in diameter) arranged transversely on suitable bearings at a distance of 60 mm from each other.

The reactor is fed with a gaseous mixture having the following composition in volume:
 oxygen: 15.13%
 nitrogen: 57.20%
 steam: 14.85%
 isobutene: 6.05%
 ammonia: 6.77%

By operating under fluidization conditions at 425° C., with a contact time of 3.9 seconds, with a linear gas velocity of 13.5 cm/sec and without applying any overpressure, a gaseous mixture is discharged from the reactor with the following composition in volume.
 oxygen: 2.05%
 nitrogen: 54.28%
 steam: 34.20%
 ammonia: 0.66%
 carbon dioxide: 2.69%
 carbon monoxide: 1.33%
 isobutene: 0.39%
 acetonitrile: 0.08%
 acrylonitrile: 0.82%
 methacrylonitrile: 3.79%
 hydrocyanic acid: 0.45%
 methacrolein: 0.06%

The isobutene conversion is thus 93.6% with a selectivity for acrylonitrile and methacrylonitrile of 81.5% with respect to the converted isobutene.

EXAMPLE 5

The run of Example 4 is repeated by delivering to the reactor a gaseous mixture having the following composition in volume:
 oxygen: 16.12%
 nitrogen: 60.85%
 steam: 12.34%
 metha xylene: 3.63%
 ammonia: 7.06%

By operating under fluidization conditions with a temperature of 420° C., with a contact time of 6.7 seconds, a linear gas velocity of 7.8 cm/sec, and without applying any overpressure, the m-xylene conversion is 87% with a selectivity for isophthalodinitrile of 78% based on the converted m-xylene.

EXAMPLE 6

The following mixture of nitrates is fused at 80° C.:

Fe(NO$_3$)$_3$.9H$_2$O—284 g
Cr(NO$_3$)$_3$.9H$_2$O—211.5 g
Al(NO$_3$)$_3$.9H$_2$O—131.8 g
Co(NO$_3$)$_2$.6H$_2$O—204.6 g
Mn(NO$_3$)$_2$.4H$_2$O—176.6 g
Zn(NO$_3$)$_2$.6H$_2$O—104.6 g
Bi(NO$_3$)$_3$.5H$_2$O—170.5 g 745 g of (NH$_4$)$_6$Mo$_7$O$_{24}$.4H$_2$O are dissolved in 1.5 liters of deionized water maintained at boiling point. 12 g of H$_3$PO$_4$ with a titre of 85% by weight, brought to pH 4 by addition of 10 wt.% aqueous ammonia, are added to the solution cooled to 80° C. There are then added to the solution 32.0 g of telluric acid dissolved in 100 ml of deionized water, 258 g of colloidal silica LUDOX AS containing 40% by weight of SiO$_2$, and 40.1 g of SbCl$_3$ dissolved in 50 ml of 10 wt.% aqueous hydrochloric acid. There are then added 2.1 g of KNO$_3$ dissolved in 50 ml of deionized water. The mixture of nitrates is gradually added to the resulting solution, operating at 80° C. After 30 minutes 10 wt.% aqueous ammonia is gradually added to the suspension, until the pH value of the suspension is 5.6. The heating is continued for a further 5 hours, while setting the pH to the above value, if necessary, by means of the addition of aqueous ammonia.

The suspension thus obtained, having a solids content of the order of 25% by weight, is submitted to drying in s spray-drier in which air is delivered at 250° C. and exited at 150° C. (the temperature of the solid in this treatment being of the order of 130° C.). The solid thus obtained consists of particles with a size of from 250 to 10 microns.

The decomposition of the ammonium salts and the nitrates is carried out by gradually bringing the temperature from the initial value of 150° C. to a value of 420° C. in a period of 20 hours, the temperature being then maintained at 420° C. for 1 hour.

The activation is carried out by gradually increasing the temperature by 20° C. per hour up to a final value of 540° C., the temperature being then maintained at 540° C. for 2 hours in the presence of air.

The catalyst thus obtained has a molar ratio between phases (I) and (II) equal 0.45:1, expressed as defined above, and an atomic ratio between promoters and the sum of the elements Me$^{II}$ and Me$^{III}$ equal to 0.37:1. Moreover, the basic element (potassium) and the acid element (phosphorus) are present in amounts equal to 0.0125 and respectively 0.083 atoms for each atom of molybdenum.

The catalyst has an apparent density of 1.15 g/ml and a specific surface area of 17.8 sq.m/g.

X-ray analysis shows the presence of phase (II) typical of alpha-manganese molybdate and beta-cobalt molybdate, and of phase (I) (isomorphous to monoclinic ferric molybdate) with a slight shifting and broadening of the bands attributable to the insertion of tellurium, antimony and bismuth into the crystalline structure. A strong absorption in the visible and near ultraviolet regions, at 480–400 nm, denotes the presence of transfer of electric charges between the ions.

EXAMPLE 7

3 ml of the catalyst prepared in Example 6 are charged into a microreactor which is fed, without applying any overpressure, with a gaseous mixture having the following composition in volume:
propylene: 7.5%
ammonia: 7.9%
air: complement to 100%

By operating at 438° C. (reckoned within the reactor) and with a contact time of 2.1 seconds, there is achieved a propylene conversion of 98.8% with a selectivity for acrylonitrile of 91% with respect to the converted propylene.

EXAMPLE 8

The following mixture of salts is fused at 50°–60° C.
Fe(NO$_3$)$_3$.9H$_2$O—156.3 g
Ce(NO$_3$)$_3$.6H$_2$O—23.6 g
Cr(NO$_3$)$_3$.9H$_2$O—40.7 g
Co(NO$_3$)$_2$.6H$_2$O—157.9 g
Ni(NO$_3$)$_2$.6H$_2$O—78.9 g
Bi(NO$_3$)$_3$.5H$_2$O—65.9 g A solution consisting of 1.37 g of KNO$_3$ in 10 ml of distilled water is added to the fused mixture, and the whole is homogenized by stirring.

A solution is formed by dissolving 287.45 g of (NH$_4$)$_6$Mo$_7$O$_{24}$.4H$_2$O in 400 ml of boiling distilled water. The temperature of the solution is brought to a value of 80° C., and, while maintaining the mass under agitation, the following substances are added in the order shown: 7.82 g (4.58 ml) of H$_3$PO$_4$ with a titre of 85% by weight, brought to pH 4 by means of the addition of 35 ml of 32 wt.% NH$_4$OH; 39.7 g (132 ml) of colloidal silica LUDOX AS containing 30 wt.% of SiO$_2$; the fused mixture of nitrates, this last addition being carried out gradually over a period of about 20 minutes.

There is thus obtained a dense, yellow precipitate with a pH value of about 1. The suspension is agitated for about 15 minutes, while maintaining the temperature at about 80° C., and a correction of the pH value is then carried out by gradually adding portions of a solution of NH$_4$OH in distilled water in a NH$_4$OH/H$_2$O weight ratio of 0.3:1. The overall addition of solution amounts to 400 ml, and the final pH value of the suspension is 5.5. The treatment at 80° C. under agitation is continued for a further 3 hours, and during this period of time the variations in pH are corrected by means of the addition of aqueous ammonia to control the pH value to 5.5.

After this period of time, the pH value is substantially stable and the dense suspension is brown in colour.

The suspension, having a solids content of the order of 25% by weight, is delivered to spray-drying apparatus, in countercurrent with hot air. In practice, the drying is carried out by using an inlet temperature of the air of 210° C., and an outlet temperature of 120° C., and there is discharged a fine powder with an average size of 1–10 microns and a moisture content of about 5% by weight.

The powder thus obtained is gradually brought to a temperature of about 380° C. over a period of 20 hours, the temperature being then maintained at this value for one hour. This treatment is carried out in an oven in the presence of air, and brings about the decomposition of the nitrates and the ammonium salts present in the solid.

After this decomposition treatment, the solid is heated in an oven at 420° C. for one hour, and then cooled down to ambient temperature. The solid thus obtained is mixed with water in a 100:5 weight ratio and formed into a cake by pressing a 300 kg/sq.cm. The cake is ground to particles with a size of 0.1–0.5 mm (140–35 mesh). Magnesium stearate is added to the powder thus obtained in an amount of 0.9% by weight, and the mass is homogenized. The powder is then formed into hollow cylinders with dimensions of 5×5 mm and a bore diameter of 1.8 mm, in a Manesty rotating compacting apparatus provided with a punch and under a load of about 2 tons. The bodies thus obtained have a surface area of 5–10 sq.m/g and a bulk density of 1.2 g/ml.

The cylinders are brought to a temperature of 250° C. over 2.5 hours, and the temperature is maintained at this value for 180 minutes to decompose magnesium stearate. This operation is carried out in air.

The activation is then carried out by heating at 530° C. for 5 hours in air.

Upon cooling, there is recovered a catalyst having the dimensions indicated above, with a surface area of 5–7 sq.m/g, a specific gravity of 1.9 g/ml and a bulk density of 1.0–1.1 g/ml.

Analysis of the catalyst shows that the latter contains beta-cobalt molybdate and beta-nickel molybdate belonging to the crystalline phase (II) (isomorphous to alpha-manganese molybdate), whereas iron, chromium and cerium are present in the catalyst in the form of the corresponding molybdates belonging to the crystalline phase (I) (isomorphous to ferric molybdate).

The molar ratio between phase (I) and phase (II) is 0.33:1, expressed as defined above.

The atomic ratio between promoter element (bismuth) and the sum of iron, cerium, chromium, cobalt and nickel, is 0.1:1. Finally, the basic element (potassium) and the acid element (phosphorus) are present in amounts equal to 0.083 and respectively 0.042 atoms for each atom of molybdenum.

Analysis by X-ray diffractometry shows the characteristic bands of beta-cobalt molybdate (an isomorph of alpha-manganese molybdate) at an interplanar distance of 3.36 A (intensity reckoned as 100), 3.81 A (intensity 25), 3.14 A (intensity 14), 3.49 A (intensity 8), and 4.65 A (intensity 8).

The characteristic bands of ferric molybdate crystallized in the monoclinic system are present at an interplanar distance 3.875 A (intensity 24, with reference to the band at 3.36 A of the phase beta-cobalt molybdate taken as 100), 3.48 A (intensity 10), 3.90 A (intensity 10), 4.08 A (intensity 10), 3.24 A (intensity 8), 4.33 A (intensity 8) and 2.955 A (intensity 6). Some bands are slightly broadened and shifted, this being attributable to the insertion of bismuth in the lattice. This is also confirmed by the gamma resonance Mössbauer spectrum. In fact, whereas pure ferric molybdate presents a sharp peak, the catalyst according to the invention presents a peak at the same isomer shift with a broader band and the presence of lateral "shoulders" attributable to the insertion of bismuth.

The electronic spectra of diffuse reflectance of the catalyst present in the visible and near ultraviolet region a higher absorption between 20,000 and 21,000 $cm^{-1}$ not attributable to the pure metallic molybdates, and deriving from the insertion of the promoter (bismuth) into phases (I) and (II).

EXAMPLE 9

340 ml of the catalyst obtained in Example 8 are charged into a tubular reactor having an inner diameter of 12.1 mm and a height of 3655 mm. The volume of the reactor is 420 ml and the ratio between apparent volume of the catalyst and volume of the reactor is 80%. The reactor is provided with a jacket in which fused salts thermostated to 370° C. are circulated.

The reactor is fed with a gaseous stream having the following composition in volume:

propylene—6.64%
oxygen—12.5%
steam—34.0%
nitrogen—complement to 100%

The reaction is carried out at a pressure of 1 kg.sq.cm, with a linear gas velocity of 155 cm/sec, with a contact time of 2.3 seconds and a hourly space velocity of 1575 $hours^{-1}$. Under these conditions the peak of temperature in the catalytic bed is 399° C. and the gaseous stream discharged from the latter has the following average composition in volume:

Oxygen—4.50%
nitrogen—47.14%
steam—41.00%
propylene—0.31%
acrolein—4.59%
acrylic acid—1.40%
acetic acid—0.04%
carbon monoxide—0.39%
carbon dioxide—0.63%

The propylene conversion is 95.3%, with a selectivity of 95.6% for the acrolein and acrylic acid produced. The output is 250 g, expressed as the sum of acrolein and acrylic acid produced per liter of catalyst and per hour.

EXAMPLE 10

The following mixture of salts is fused at 80° C.:
$Fe(NO_3)_3.9H_2O$—142 g
$Cr(NO_3)_3.9H_2O$—141 g
$Co(NO_3)_2.6H_2O$—204.6 g
$Mn(NO_3)_2.4H_2O$—176.5 g
$Bi(NO_3)_3.5H_2O$—170.5 g 745 g of ammonium paramolybdate are dissolved in two liters of deionized water at 95° C. The solution is cooled down to 80° C. and there are added 3 g of phosphoric acid with a titre of 85% by weight, diluted with 50 ml of deionized water. There are then added 35.3 g of $Sb_2O_3$ dissolved in 90 ml of 10 wt.% aqueous HCl, and 25 g of colloidal silica LUDOX AS containing 40 wt.% of $SiO_2$. There are then added 17.8 g of $KNO_3$ dissolved in 100 ml of deionized water heated at 80° C.

The mixture of fused nitrates is then added to the aqueous mass maintained under agitation, over a period of 20 minutes, while maintaining the temperature at about 80° C. There is thus obtained a suspension having a pH value of 1.5, to which 30 wt.% aqueous $NH_4OH$ is gradually added to bring the pH to a value of 5.5.

The mass is maintained at a temperature of 80° C. for a further 4 hours, while controlling the pH value to 5.5 by means of suitable additions of ammonia. The suspension, having a solids content of the order of 25% by weight, is dried in a spray-drier, thus obtaining granules with a size of 1–10 microns.

The nitrates and the ammonium compounds are then decomposed by gradually bringing the temperature from an initial value of 120° C. to a final value of 380° C., using an increase in temperature of 20° C. per hour. The temperature is then brought to 420° C., and maintained at this value for one hour.

The solid particles thus treated are admixed with water in an amount of 5% by weight in a Werner mixer. The mixture is then compacted at 360 kg/sq.cm, and the compacted mass is formed into granules with a size of 0.1–0.5 mm.

Magnesium stearate is then added in an amount of 1% by weight, and the granules are formed into hollow cylinders with dimensions of 5×5 mm and a bore diameter of 1.8 mm in a Manesty apparatus provided with a punch, under a load of about 2 tons. The hollow bodies thus obtained are heated at 250° C. for three hours to decompose magnesium stearate.

The bodies are then activated by gradually increasing the temperature by 100° C. each hour, up to 550° C., and the temperature is maintained at this value for 3 hours. There is thus obtained a catalyst in the form of hollow cylinders, with a surface area of 6 sq.m/g and a bulk density of 1.1 g/ml.

The molar ratio between phase (I) and phase (II) in the catalyst is 0.25:1, expressed as defined above, and the atomic ratio between the promoters and the sum of the metals $Me^{II}$ and $Me^{III}$ is 0.2:1. Moreover, the basic element (potassium) and the acid element (phosphorus) are present in an amount of 0.04 and respectively 0.08 atoms for each atom of molybdenum.

Analysis by X-ray diffractometry shows the presence of crystals well differentiated belonging to the alpha manganese molybdate phase and to the beta cobalt molybdate phase, which is an isomorph of the former. The phase belonging to the family of ferric molybdate is present in the form of small crystals having broadened bands with a slight shifting with respect to pure ferric molybdate. Said phenomena of broadening and shifting of the bands are attributable to the insertion of bismuth and antimony ions in the crystalline lattice. The ultraviolet and visible spectrum shows in the zone of transfer of electronic charges at 450–500 nm a strong absorption attributable to the insertion of bismuth and antimony in the active phase of the catalyst.

EXAMPLE 11

The catalyst prepared in Example 10 (330 ml) is charged into a fixed bed reactor having an inner diameter of 12.1 mm and a height of 3655 mm. The reactor is thermostated by circulating fused salts in a jacket. Operating at 360° C. without applying any overpressure, at a linear gas velocity of 160 cm/sec and with a contact time of 2.2 seconds, there is passed through the catalyst a gaseous mixture having the following composition in volume:

isobutylene—4.3%
oxygen—8.5%
steam—15.0%
nitrogen—72.2%

The gaseous stream discharged from the reactor has the following average composition in volume:

nitrogen—74.05%
oxygen—2.38%
isobutylene—0.23%
steam—18.89%
formaldehyde—0.18%
acetaldehyde—0.05%
acetic acid—0.10%
methylacrolein—2.94%
methacrylic acid—0.08%
carbon monoxide—0.32%
carbon dioxide—0.88%

The isobutylene conversion is 94.6%, with a selectivity for methylacrolein and methacrylic acid of 74.2% with respect to the converted isobutylene.

EXAMPLE 12

The following nitrates are dissolved at 80° C. in their water of crystallization:
Fe(NO$_3$)$_3$.9H$_2$O—54.9 g
Cr(NO$_3$)$_3$.9H$_2$O—81.4 g
Ce(NO$_3$)$_3$.6H$_2$O—59.0 g
Mn(NO$_3$)$_2$.4H$_2$O—68.2 g
Co(NO$_3$)$_2$.6H$_2$O—79.0 g
Cd(NO$_3$)$_2$.4H$_2$O—41.9 g
Bi(NO$_3$)$_3$.5H$_2$O—66 g 287.5 g of (NH$_4$)$_6$Mo$_7$O$_{24}$.4H$_2$O are dissolved in 500 ml of deionized water at 95° C., the solution is cooled to 80° C. and there are added to the latter 12 g of H$_3$PO$_4$ with a titre of 85% by weight, brought to pH 4 by means of the addition of 35 wt.% aqueous ammonia. There are then added 62.4 g of telluric acid dissolved in 100 ml of deionized water, 52 g of colloidal silica LUDOX AS containing 30% by weight of SiO$_2$, and 1.4 g of KNO$_3$ dissolved in 10 ml of deionized water. The solution of nitrates heated at 80° C. is gradually added to the resulting aqueous solution maintained at 80° C. After 30 minutes 10 wt.% aqueous ammonia is gradually added to the resulting suspension, until the pH is brought to a final value of 5.4. The suspension is heated at 80° C. for a further 4 hours, while controlling the pH value within the range 5–5.5.

Water is gradually evaporated from the suspension maintained under efficient agitation, and the drying is completed in an oven at 130° C. until the water content is reduced to a value of 5% by weight.

The product thus obtained is finely ground and the powder is sieved on a 325 mesh screen with separation of the particles with a size lower than about 44 microns. The nitrates and the ammonium salts are decomposed by bringing the temperature from an initial value of 150° C. to a final value of 420° C. in 20 hours, and maintaining the temperature at 420° C. for one hour. The powder humidified with 5% by weight of water is formed into a cake by compression at 400 kg/sq.cm, and the cake is reduced into particles with a size of 0.1–0.5 mm. The particles are formed into hollow cylinders as in Example 8, and the latter are heated at 550° C. for 4 hours.

The catalyst thus obtained has a bulk density of 1 g/ml and a surface area of 8.3 sq.m/g.

The molar ratio between phase (I) and phase (II) in the catalyst is 0.35:1, expressed as defined above. Moreover, the atomic ratio between promoters and the sum of the elements $Me^{II}$ and $Me^{III}$ is 0.353:1. The basic element (potassium) and the acid element (phosphorus) are present in an amount of 0.0083 and respectively 0.042 atoms for each atom of molybdenum.

X ray analysis of the catalyst shows the presence of the phase (II) (an isomorph of alpha-manganese molybdate) and the phase (II) (an isomorph of monoclinic ferric molybdate) with a broadening and shifting of the bands attributable to the insertion of tellurium and bismuth in said crystalline phases. In the visible and near ultraviolet region there is noted a strong absorption in the zone of transfer of electric charges (at 480–500 nm).

EXAMPLE 13

6 ml of the catalyst prepared in Example 12 are charged into a reactor which is operated without applying any overpressure, at 390° C. (as measured within the catalytic bed). A gaseous mixture having the following composition in volume is circulated through the catalyst:

propylene—5.6%
oxygen—13.0%
steam—32.1%
nitrogen—complement to 100%

By using a contact time of 2.5 seconds and the other reaction conditions indicated above, the propylene conversion is 96.8% with an overall selectivity for acrolein and acrylic acid of 92.5%, based on the converted propylene.

EXAMPLE 14

The run of Example 13 is repeated by using the catalyst of Example 12 and a gaseous mixture having the following composition in volume:
- butene-1—3.8%
- steam—27.0%
- oxygen—7.0%
- nitrogen—balance to 100%

By operating at 370° C., without applying any overpressure and with a contact time of 2 seconds, 97% of the butene-1 fed in are converted into butadiene.

EXAMPLE 15

The following mixture of salts is fused at 80° C.:
- $Fe(NO_3)_3.9H_2O$—213.10 g
- $Co(NO_3)_2.6H_2O$—230.15 g
- $Ni(NO_3)_2.6H_2O$—127.75 g
- $KNO_3$—1.80 g A solution is prepared by dissolving into one liter of deionized water, heated at 95° C., the following compounds:
- ammonium paramolybdate—372.35 g
- 85 wt.% phosphoric acid—10.13 g
- colloidal silica LUDOX AS ($SiO_2$ content of 40%)—35.65 g The mixture of fused nitrates is poured over 20 minutes into said solution heated at 80° C. and maintained under agitation.

A dense precipitate is obtained with a pH value of 1.5, to which 30% aqueous $NH_4OH$ solution is gradually added until the pH is brought to a value of 5.5.

The suspension is heated at 80° C. for a further 4 hours, while setting the pH value to 5.5 by means of the possible addition of ammonia. The suspension is then dried by spray-drying.

The nitrates and the ammonium compounds are then decomposed by gradually heating from an initial temperature of 120° C. to a final temperature of 380° C., with an increase in temperature of 20° C. per hour. The temperature is then brought to 420° C. and maintained at this value for one hour.

After cooling to ambient temperature, the powder thus obtained is impregnated in a Werner mixture with a solution of 92.8 g of $Bi(NO_3)_3.5H_2O$ in 200 ml of water containing also 17.28 g of $SnCl_2 2H_2O$.

After thorough homogenization in the mixer, the mass is gradually dried at 80° C. for 12 hours, and then compacted and formed into granules, and admixed with 1.5% by weight of magnesium stearate. The granules are formed into hollow bodies with dimensions 5×5×2 mm.

The bodies thus obtained are heated at 250° C. for three hours to decompose the stearate, and are then activated by gradually increasing the temperature by 100° C. per hour, up to 540° C. The temperature is then maintained at this last value for 4 hours.

The hollow bodies thus obtained have a surface area of 5.1 sq.m/g and a bulk density of 1.05 g/ml. X-ray diffractometry analysis shows the presence of crystals with structures belonging to the beta-cobalt molybdate and ferric molybdate phases, without any bands attributable to other compounds.

EXAMPLE 16

340 ml (357 g) of the catalyst prepared in Example 15 are charged into a fixed bed reactor having an inner diameter of 12.1 mm and a height of 400 mm. The reactor is thermostated by circulating fused salts in a jacket.

Operating at a pressure of 2.10 ATA at the inlet and 2.00 ATA at the outlet of the reactor, with a linear gas velocity of 155 cm/sec and with a contact time of 2.50 seconds, a gaseous mixture is delivered to the reactor with the following composition in volume:
- propylene—6.6%
- oxygen—12.5%
- nitrogen—47.0%
- steam—33.9%

By using an outer temperature of 362° C. and a peak temperature of 395° C., the gaseous stream discharged from the reactor has the following average composition in volume:
- nitrogen—47.30%
- oxygen—4.38%
- steam—40.96%
- CO—0.39%
- $CO_2$—0.63%
- propylene—0.30%
- acrolein—4.60%
- acrylic acid—1.40%
- acetic acid—0.04%

The propylene conversion is 95.45% with a selectivity for acrolein and acrylic acid of 95.25% with respect to the converted propylene.

EXAMPLE 17

The following mixture of salts is fused at 80° C.:
- $Fe(NO_3)_3.9H_2O$—663.42 g
- $Co(NO_3)_2.6H_2O$—318.62 g
- $Ni(NO_3)_2.6H_2O$—106.11 g
- $Bi(NO_3)_3.5H_2O$—177.01 g
- $KNO_3$—3.70 g 773.2 g of ammonium paramolybdate, 21.04 g of 85 wt.% phosphoric acid and 74.0 g of colloidal silica LUDOX AS containing 40% of $SiO_2$, are dissolved in 2 liters of water.

The mixture of fused nitrates is poured into said solution maintained at 80° C. and under agitation. A precipitate forms in the medium which has a pH value of 1.5, and a 30% aqueous solution of $NH_4OH$ is gradually added to set the pH value to 5.5. This is followed by a heat treatment at 80° C. for 4 hours, while controlling the pH value to 5.5.

The suspension is then dried in a spray-drier, and the powder thus obtained is gradually heated up to 420° C. to decompose the nitrates. The temperature is then maintained at 420° C. for one hour. Upon cooling, the powder is moistened, compacted, granulated, dried and admixed with 1% by weight of magnesium stearate. The granules are then formed into hollow bodies with dimensions 5×5×2 mm. The stearate is then decomposed by bringing the temperature from 120° to 250° C. over 4 hours. The bodies are then activated by bringing the temperature from 250° C. to 540° C. in 3 hours, and calcined at 540° C. for 5 hours.

The catalyst thus obtained has the following composition, referred to the metals:

$Mo_{12}Fe_{4.5}Co_3Ni_1Bi_1K_{0.1}P_{0.5}Si_{1.35}Mg_{0.06}$.

The catalyst has a surface area of 2.0 sq.m/g and a bulk density of 1.3 g/ml.

X-ray diffractometry shows the presence of the beta-cobalt molybdate phase and the ferric molybdate phase, with a distortion due to the insertion of bismuth.

EXAMPLE 18

360 ml of the catalyst prepared in Example 17 are charged into a fixed bed reactor with an inner diameter of 12.1 mm and a height of 4,000 mm, thermostated by circulating fused salts in a jacket. Operating at a pressure of 1.7 ATA at the inlet and 1.5 ATA at the outlet, with a linear gas velocity of 158 cm/sec, with a contact time of 2.50 seconds and an external temperature of 376° C. (peak temperature 390° C.), a gaseous mixture is delivered to the reactor with the following composition in volume:

isobutene—6.60%
oxygen—12.46%
nitrogen—80.94%

The isobutene conversion is 97.9% with a selectivity for methacrolein and methacrylic acid of 84% with respect to the converted isobutene.

We claim:

1. A catalyst active and selective in the conversation of unsaturated hydrocarbons into diolefins and unsaturated nitriles and aldehydes, which comprises:
    a crystalline phase (I) consisting of one or more molybdates of the monoclinic system, selected from the group consisting of ferric molybdate, an aluminum molybdate isomorph of ferric molybdate, a cerium molybdate isomorph of ferric molybdate, and a chromium molybdate isomorph of ferric molybdate; and
    a crystalline phase (II) consisting of one or more molybdates belonging to the monoclinic system, selected from the group consisting of alpha manganese molybdate, a beta cobalt molybdate isomorph of alpha manganese molybdate, a beta nickel molybdate isomorph of alpha manganese molybdate, a zinc molybdate isomorph of alpha manganese molybdate, a magnesium molybdate isomorph of alpha manganese molybdate, and a cadmium molybdate isomorph of alpha manganese molybdate,
    wherein the molar ratio between the molybdates of phase (I) and molybdates of phase (II) is from 0.1:1 to 5:1, and
    one or more promotor chemical elements selected from the group consisting of selenium, tellurium, arsenic, antimony, bismuth, vanadium, niobium, tin, lead and thallium, homogenously distributed with said crystalline phases (I) and (II) with distortion of the structure of said phases and without creating new further phases wherein the atomic ratio between said promotor elements and the sum of said bivalent and trivalent elements of phases (I) and (II) in said catalyst is from 0.01:1 to 1.0:1.

2. The catalyst of claim 1, wherein said molar ratio is from 0.2:1 to 1:1.

3. The catalyst of claim 1, wherein said atomic ratio is from 0.05:1 to 0.5:1.

4. The catalyst of claim 1, which further comprises alkaline elements selected from the group consisting of potassium, lithium, cesium and magnesium and/or acidic elements selected from the group consisting of phosphorus and silicon in an amount of from 0.005 to 0.5 atoms for each atom of molybdenum.

5. The catalyst of claim 1, which further comprises amorphous silica as a diluent in an amount not exceeding 50% by weight of the overall weight of said catalyst.

6. The catalyst of claim 1, which further comprises amorphous silica as a support in an amount not exceeding 80% by weight of the overall weight of said catalyst.

7. The catalyst of claim 5, wherein said amount of diluent does not exceed 20% by weight of the overall weight of said catalyst.

8. The catalyst of claim 1, in the form of granules suitable for use as a fluid bed, with an average size of from 5 to 200 microns, an apparent density of from 0.6 to 1.2 g/ml and a specific surface area of from 10 to 150 m$^2$/g.

9. The catalyst of claim 1, wherein said specific surface area is from 15 to 110 m$^2$/g.

10. The catalyst of claim 1, in the form of bodies suitable for use as a fixed bed, said bodies being obtained by forming a powder of said catalyst to the desired shape, with an apparent density of from 0.8 to 1.5 g/ml and a specific surface area of from 1 to 10 m$^2$/g.

11. A process for preparing a catalyst according to claim 1, which comprises the following steps of:
    precipitating said molybdates of phases (I) and (II) from an aqueous solution of ammonium paramolybdate and nitrates of said bivalent and/or trivalents metals, while bringing the pH value from an initial value of about 1 to a final value of about 5.5.
    drying the precipitate thus obtained to reduce its water content to values not exceeding 5–10% by weight;
    heat treating the dried precipitate at a temperature of from 250° to 420° C. for a period sufficient to decompose substantially completely the ammonium and nitrate anions present therein; and
    activating the product thus obtained at a temperature of from 500° to 750° C.

12. The process of claim 11, wherein said aqueous solution comprises one or more promoter elements chosen from selenium, tellurium, arsenic, antimony, bismuth, vanadium, niobium, tin, lead and thallium in the form of acids, oxides and/or nitrates.

13. The process of claim 11, wherein said precipitation is carried out at a temperature of from 20° to 130° C., the pH being brought to said final value by means of the addition of aqueous ammonia solution.

14. The process of claim 11, wherein said drying is carried out at a temperature of from 100° to 180° C.

15. The process of claim 11, wherein said heat treatment is carried out by gradually bringing the temperature to a preselected value within the range 250° to 420° C. in a period of from 3 to 20 hours, and maintaining the temperature at said preselected value for a period of from 1 to 2 hours.

16. The process of claim 11, wherein said activation is carried out at a temperature of from 500° to 600° C. for a period of from 2 to 8 hours.

17. The process of claim 11, wherein the solution contains a soluble silicate in an amount such as obtain a final content of amorphous silica in the catalyst not exceeding 50% by weight.

18. The process of claim 11, wherein said precipitate is submitted to a spray-drying with reduction into granules of from 1 to 10 microns, the granules are submitted to the heat treatment, and then saturated with water and formed into a cake with subsequent drying, grinding to particles of from 0.1 to 1 mm, admixture with one or more lubricants and compaction into bodies suitable for use as a fixed bed, said bodies being then submitted to the activation treatment.

19. The process of claim 17, wherein the precipitate is submitted to a spray-drying under such conditions as to obtain granules with an average size of about 5 to 200 microns.

* * * * *